(12) United States Patent
Lindstrom et al.

(10) Patent No.: US 8,691,153 B2
(45) Date of Patent: Apr. 8, 2014

(54) FLUORESCENCE READER

(75) Inventors: Tomas Lindstrom, Stockholm (SE); Ib Mendel-Hartvig, Uppsala (SE); Ove Öhman, Uppsala (SE); Johan Backlund, Gothenburg (SE); Kennet Vilhelmsson, Ojersjo (SE)

(73) Assignee: Johnson & Johnson AB, New Brunswick, NJ (US)

( * ) Notice: Subject to any disclaimer, the term of this patent is extended or adjusted under 35 U.S.C. 154(b) by 1478 days.

(21) Appl. No.: 11/726,973

(22) Filed: Mar. 22, 2007

(65) Prior Publication Data

US 2007/0231883 A1 Oct. 4, 2007

(30) Foreign Application Priority Data

Mar. 22, 2006 (SE) ...................................... 0600642

(51) Int. Cl.
*G01N 21/01* (2006.01)
*G01N 21/64* (2006.01)
*G01N 21/76* (2006.01)

(52) U.S. Cl.
USPC ........................ 422/82.11; 422/52; 422/82.08

(58) Field of Classification Search
USPC ............................ 422/82.06, 82.11, 52, 82.08
See application file for complete search history.

(56) References Cited

U.S. PATENT DOCUMENTS

| 3,973,129 A * | 8/1976 | Blumberg et al. ......... 250/461.2 |
| 4,956,150 A * | 9/1990 | Henry ........................... 422/102 |
| 4,997,278 A | 3/1991 | Finlan et al. |
| 5,158,720 A * | 10/1992 | Levy ............................... 264/21 |
| 5,344,784 A * | 9/1994 | Attridge ......................... 436/518 |
| 5,399,499 A * | 3/1995 | Paz-Pujalt et al. ............ 436/165 |
| 5,619,601 A * | 4/1997 | Akashi et al. .................... 385/16 |
| 5,757,014 A | 5/1998 | Bruno et al. |
| 5,811,312 A | 9/1998 | Hasegawa et al. |
| 5,885,527 A * | 3/1999 | Buechler ......................... 422/58 |
| 6,143,576 A | 11/2000 | Buechler |
| 6,156,270 A | 12/2000 | Buechler |
| 6,657,236 B1 | 12/2003 | Thibeault et al. |
| 6,710,870 B1 * | 3/2004 | Marowsky et al. ........... 356/317 |
| 6,767,510 B1 | 7/2004 | Buechler |
| 6,787,110 B2 * | 9/2004 | Tiefenthaler .................... 422/91 |

(Continued)

FOREIGN PATENT DOCUMENTS

| CN | 1423842 A | 11/2003 |
| JP | 1-138443 A | 5/1989 |

(Continued)

OTHER PUBLICATIONS

Supplemental European Search Report for International Patent Application No. EP07716079 (Sep. 14, 2012).

(Continued)

*Primary Examiner* — Paul Hyun
(74) *Attorney, Agent, or Firm* — Hiscock & Barclay, LLP (57) ABSTRACT

A fluorescence reader for an optical assay arrangement includes a polymeric sample substrate having a reaction site-surface and a substrate surface. A light source is arranged to illuminate the reaction site-surface through the substrate surface, and a detector device is arranged to detect fluorescent light emitted from the reaction site-surface and transmitted through the substrate surface, the substrate surface provided, for example, as a light-collecting body to allow fluorescent light rays exceeding a critical emission angle for total internal reflection to escape the substrate and enter the body.

31 Claims, 8 Drawing Sheets

(56) References Cited

U.S. PATENT DOCUMENTS

| | | |
|---|---|---|
| 2003/0035758 A1 | 2/2003 | Buechler et al. |
| 2004/0077103 A1 | 4/2004 | Buechler |
| 2004/0126767 A1 | 7/2004 | Anderberg et al. |
| 2005/0136552 A1 | 6/2005 | Buechler |

FOREIGN PATENT DOCUMENTS

| | | |
|---|---|---|
| JP | 7-120397 A | 5/1995 |
| JP | 2005-515424 A | 5/2005 |
| WO | WO-99/46596 A1 | 9/1999 |
| WO | WO 01/41225 A2 | 6/2001 |
| WO | WO-01/57501 A1 | 8/2001 |
| WO | 03/060446 A1 | 7/2003 |
| WO | WO-03/103835 A1 | 12/2003 |

OTHER PUBLICATIONS

Chinese Office Action for 201210123087.2; dated Dec. 24, 2013; 20 pages.

* cited by examiner

FLUORESCENCE READER

CROSS REFERENCE TO RELATED APPLICATION

This U.S. application claims priority to Swedish Patent Application No. SE-0600642-3, filed Mar. 22, 2006, the contents of which are hereby incorporated by reference into the present disclosure in their entirety.

TECHNICAL FIELD OF THE INVENTION

The present invention relates to an improved fluorescence/phosphorescence reader for a sample substrate in an optical assay arrangement. The invention also relates to the use of said fluorescence/phosphorescense reader, and to a sample substrate adapted for said fluorescence reader.

BACKGROUND OF THE INVENTION

Analytical and diagnostic determinations can be performed on liquid samples by means of optical assays based on the detection of analytes in a sample, such as e.g. nucleic acids, peptides, proteins, antibodies, hormones, or drugs. One important application of optical assays is the field of immunology, in which the analyte is detected with the aid of a specific antibody, which is capable of binding to the analyte to form optically detectable complexes, e.g. by labeling the analyte with a fluorophore, or by providing a fluorophore-labeled antibody before the optical detection. The detection of the fluorophores may be performed by means of a fluorescence reader, which is capable of illuminating the assay support substrate with an exciting light source and of detecting the fluorescent light emitted from the fluorophores.

An optical assay involving detection of fluorescent light emitted from fluorophores is performed by an optical assay arrangement comprising a sample supporting substrate and a fluorescence reader. The fluorescence reader comprises a source and detector for electromagnetic radiation within the optical wavelength region (i.e. between approximately 40 nm and 1 mm), and suitable optical filters and wave-guiding means. The sample support comprises a substrate of e.g. a polymeric material having a high optical transmittance in the wavelength ranges of the exciting light and of the emitted light, and may also have a high absorbance of other wavelengths. The substrate is provided with one or more reaction site areas, comprising spots and/or lines of probe molecules, e.g. of an antibody, providing binding sites for molecules of the analyte, i.e. the target molecules, that may be present in a sample. The substrate may further be provided with a pattern of protruding microstructures forming e.g. micro pillars or micro posts, which may be arranged to form a capillary flow path for the sample.

When the sample is brought in contact with the capture molecules on the support surface, and the fluorescent or phosphorescent antibody detection conjugate, optically detectable spots or lines will be formed. Fluorescent or phosphorescent light will be emitted when the substrate is illuminated with the exciting light source of the fluorescence reader, thereby indicating that a reaction has occurred between the target molecules of the sample and the probe molecules of the reaction sites. Fluorescence and phosphorescence may be defined as the emission of electromagnetic radiation resulting from absorbed exciting electromagnetic radiation, the fluorescent light lasting less than $1\times10^{-8}$ s after the excitation, and phosphorescent light lasting longer, i.e. is decaying more slowly after the exposure to the exciting light.

In fluorescence (and phosphorescence), the exciting radiation normally has a shorter wavelength (i.e. higher energy) than the emitted radiation, although the reverse may be true for multi-photon fluorescence. The fluorescent behaviour may be studied in a steady state or time-resolved, and fluorescence spectroscopy involves e.g. single- and multi-photon fluorescence, FRET (fluorescence resonance energy transfer), and fluorescence up-conversion. In fluorescence assays, the wavelength of the exciting and the emitted radiation depends on the type of fluorophore, which may be of an organic or inorganic origin, e.g. cyanine dyes, fluorescin dyes or nanocrystals. As an example, the common fluorophore Cy-5™ (GE Healthcare) is typically excited with 649 nm, and the emitted light is measured at 670 nm. The difference in wavelength between the excitation maxima and the emittance maxima is commonly referred to as the Stokes shift.

In optical assays, the concentration of an analyte in the sample may be determined by measuring the intensity of emitted fluorescent or phosphorescent light, by means of the detector device of a fluorescence reader, thereby enabling quantitative measurements. Consequently, the efficiency of the illumination of a reaction site area with exciting light, as well as the efficiency of the collection of the emitted fluorescent light, will have an effect on the performance of the optical assay.

Further, the reaction sites on a substrate surface may be provided with an array of spots or lines of different probe molecules, binding different target molecules. Therefore, a fluorescence reader may be designed to be capable of determining the presence of several analytes in a sample, by means of different fluorophores, or by using space separation of the probe molecules.

A fluorescence reader can be arranged to perform the detection of fluorescent emitted light by scanning the reaction site area or to detect an image of the entire reaction-site area as a two-dimensional array of pixels. A scanning fluorescence reader scans the surface of the sample substrate by a relative movement between the optical means and the sample substrate, and the optical means preferably comprises a narrow-band exciting light source, such as a laser, a LED or a white light source provided with spectral filters, from which the light is focused on each individual detection site. The emitted fluorescent light from each detection site is focused on an optical detector, such as e.g. a photodiode or a PMT (photo-multiplier tube). An imaging fluorescence reader is capable of detecting a two-dimensional array of pixels and the optical means comprises an exciting light source for illuminating a large part of the surface area (or the entire surface area) of the sample substrate, and a detector capable of detecting emitted light from the entire detection site-area simultaneously, e.g. a CCD (Charged-Coupled Device)-imager, which utilizes MOS (Metal-On-Semiconductor)-technology.

An optical reader is described in WO 01/575501, which discloses optical imaging of an analyte containing sample on a transparent substrate. The optical reader comprises an exciting energy source to stimulate emission of detectable light from the sample, and the substrate is provided with a reflective surface located below the sample to reflect the emitted light into the detection means.

A light detecting optical device is disclosed in WO 99/46596, comprising a light conducting body coupled to a slide, thereby improving the light collecting efficacy.

WO 03/103835 describes sample substrates provided with protruding micro posts arranged to form a capillary flow path for the sample.

It is an object of this invention to provide an improved fluorescence/phosphorescence reader capable of an efficient illumination of the reaction site area of the substrate and an efficient collection and detection of the emitted light, thereby achieving a high performance optical assay arrangement.

DESCRIPTION OF THE INVENTION

These and other objects are achieved by the fluorescence reader and sample substrate described herein.

A fluorescence reader for a sample substrate having a reaction site-surface and an opposing substrate surface is described. The fluorescence reader comprises an exciting light source positioned to inject exciting light rays into the substrate surface, and a detector device positioned to detect the fluorescent light emitted from the reaction site surface and transmitted through the substrate surface. The substrate surface is provided with total-internal-reflection-suppressing means located in the optical path of the emitted fluorescent light to increase the transmission through the substrate surface for detection by the detection device, and the total-internal-reflection suppressing means may be arranged to release emitted fluorescent light trapped within the substrate for detection by the detection device.

Further, the light source may be arranged to inject exciting light rays into the substrate surface with an incidence angle measured relative to the normal of the reaction site surface substantially coinciding with the maximum emission angle of the emitted fluorescent light. Thus, the substrate surface may be provided with incidence-angle-controlling means located in the optical path of the exciting light rays.

The incidence-angle-controlling means may include a surface relief structured entry-section designed to admit exciting light into the substrate with an enlarged incidence angle relative the normal to the reaction site surface, and the relief structure may comprise a diffractive or a refractive structure.

The total-internal-reflection suppressing means may include a surface relief-structured exit-section designed to diffract or refract the emitted fluorescent light rays out of the substrate, and it may further be designed to focus the emitted light rays, the surface relief structured exit section comprising a diffractive or a refractive structure.

The design of the surface relief structure may be arranged to vary over the surface of the exit-section in correspondence with the varying emission angle of the impinging fluorescent light, and the position and extension of the exit-section may determine the position and extension of the analysed reaction site area.

Additionally, a light collecting lens device may be positioned to receive the emitted fluorescent light transmitted through the substrate surface. Alternatively, a light-collecting body may by located in close proximity to a surface relief structured exit section provided on said substrate surface.

The total-internal-reflection suppressing means may include a light-collecting body positioned in optically wetting contact with said substrate surface.

The light-collecting body may be designed to collect and transmit light by means of total-internal-reflection, and may be substantially ellipsoid-shaped. It may also be provided with an input port for the exciting light, and/or at least one output port, and the refractive index may substantially correspond to, or be larger than, the refractive index of the substrate.

The total-internal-reflection suppressing means may, alternatively, comprise an optically wetting layer having a suitable refractive index, and at least a portion of said optically wetting layer may be attached to a lens device arranged to focus the emitted fluorescent light on the detector device. The refractive index may be higher than the refractive index of the substrate, and lower than the refractive index of the lens device. Further, at least a portion of said optically wetting layer may be attached to the detector device. The incidence angle controlling means may also comprise an optically wetting layer having a suitable refractive index, and the optically wetting layer may comprise a soft polymeric material.

Further, the detector device may be provided with spectral filtering means arranged to prevent detection of the wavelengths of the exciting light, and/or with polarization filtering means.

The light source may also be provided with spectral filtering means arranged to prevent transmission of the wavelengths coinciding with the fluorescence emission, and the excitation and the measurement of the emission may be performed in different geometrical planes.

The use of the fluorescence reader in an optical assay arrangement is also described.

A sample substrate with a reaction site surface and an opposing substrate surface where the sample substrate is adapted for a fluorescence reader is described.

The sample substrate may be made of a polymeric material, and the reaction site surface may be arranged to form lines and/or spots of fluorophores. Further, the reaction site surface may be provided with a pattern of protruding microstructures, e.g. micro posts enabling a capillary flow.

The substrate surface may be provided with a surface relief structured exit section configured to suppress the total internal reflection of emitted fluorescence light rays, and/or with a surface relief structured entry section configured to enlarge the incidence angle of the exciting light rays, the surface reliefs comprising a diffractive or a refractive structure.

Also described is a method of detecting the fluorescence of a sample substrate using a fluorescence reader. The method includes injecting exciting light rays into a substrate site surface with a light source positioned to inject exciting light rays into the substrate surface wherein the substrate surface is opposed to a reaction site-surface. The method further includes detecting fluorescent light emitted from the reaction-site surface with a detector device positioned to detect the fluorescent light emitted from the reaction site-surface and transmitted through the substrate surface wherein the substrate surface is provided with a total-internal-reflection-suppressing means located in an optical path of the emitted fluorescent light to increase transmission through the substrate surface for detection by the detector device wherein the fluorescence reader is positioned in an optical assay arrangement.

Other features and further advantages of the invention will be apparent from the non-limiting embodiments of the invention disclosed in the following description and figures, as well as from the appended claims.

BRIEF DESCRIPTION OF THE DRAWINGS

The present invention will now be described in more detail and with reference the drawings, of which.

DESCRIPTION OF PREFERRED EMBODIMENTS

The term "fluorescence reader" is defined as a reader capable of exciting and detecting both fluorescent and phosphorescent light, and the term "fluorescent light" is defined to hereinafter refer to both fluorescent and phosphorescent light. Other terms and expressions used in the description and in the claims are meant to have the meaning normally used by a person skilled in the art.

An improved performance is achieved in an optical assay arrangement comprising a polymeric sample substrate having a reaction site surface provided with a fluorophoric layer, the fluorophores forming e.g. lines or spots on the surface, and an opposing substrate surface, by means of a fluorescence reader according to the invention. The fluorescence reader comprises an exciting light source, e.g. a LED positioned to illuminate the substrate surface, and a detector, e.g. a photodiode, arranged to detect the fluorescent light emitted from the fluorophoric layer. The detector is positioned to collect and detect the emitted fluorescent light transmitted through the substrate surface, and the light source is arranged to inject exciting light into the substrate surface.

A light ray impinging on a surface will be specularly reflected from said surface when the angle of incidence of the light ray relative the normal to the surface exceeds the critical angle for total internal reflection, which depends on the relationship between the refractive index of the material on both sides of the surface. The refraction of the light ray passing from a first medium, having the refractive index n1, into a second medium, with refractive index n2, is defined by the well-known relationship of Snell's Law:

$$n1 \times \sin \alpha_{in} = n2 \times \sin \alpha_{ref} \quad (1)$$

$\alpha_{in}$ is the angle to the surface normal of the light ray in the first medium impinging on the surface between the first and the second medium, and $\alpha_{ref}$ is the angle to the surface normal of the refracted light ray propagating in the second medium. When $\alpha_{ref}=90$ degrees, total internal reflection occurs on the surface, and $\sin \alpha_{ref}=1$. From the relationship (1) above, it follows that:

$\sin \alpha_{in} = n2/n1 \times \sin \alpha_{ref} => \sin \alpha_{in(TIR)} = n2/n1 => \alpha_{in(TIR)} = \sin^{-1}(n2/n1)$, where $\alpha_{in(TIR)}$ indicates the critical angle for total internal reflection.

Thus, total-internal-reflection occurs when n1 is larger than n2 and $\alpha_{in}$ exceeds the critical angle for total internal reflection, i.e. $\alpha_{in} \geq \alpha_{in(TIR)}$ In a conventional fluorescence reader suitable for a dielectric substrate provided with a fluorophoric layer, most of the light emitted from the fluorophoric layer will be directed into the substrate, and a large portion of this emitted fluorescent light will impinge on the substrate surface with an angle exceeding said critical angle for total internal reflection. When a conventional polymeric substrate is used, with a typical refractive index between 1.5 and 1.6, total internal reflection will occur, and a large fraction of the emitted light will be trapped within the substrate, i.e. undergo multiple total internal reflections, thereby not reaching the detector.

According to this invention, total-internal-reflection suppressing means is provided on the substrate surface to release the trapped fluorescent light from the substrate, thereby allowing a larger fraction of the emitted fluorescent light to reach the detector. The total-internal-reflection suppressing means is configured to diffract or refract the light rays, or to remove the difference in refractive index. Thereby, emitted fluorescent light rays having an angle relative the normal to the substrate surface that exceeds the critical angle for total internal reflection will be allowed to escape through the surface, and reach the detector.

The exciting light rays from a light source propagating in air and impinging on the surface of the polymeric substrate will be refracted into the substrate with a direction given by the relationship (1), from which it follows that:

$\sin \alpha_{ref} = n1/n2 \times \sin \alpha_{in}$, where $\alpha_{ref}$ is the angle between the refracted light ray within the substrate and the surface normal, and $\alpha_{in}$ is the angle between the impinging light ray in air and said surface normal. Consequently, the angle of the refracted light is limited by the fact that n1/n2 will be approximately 1/1.55=0.65, and that $\alpha_{in}$ will be less than 90 degrees, resulting in that $\alpha_{ref} \leq 40$ degrees.

Figure 1:
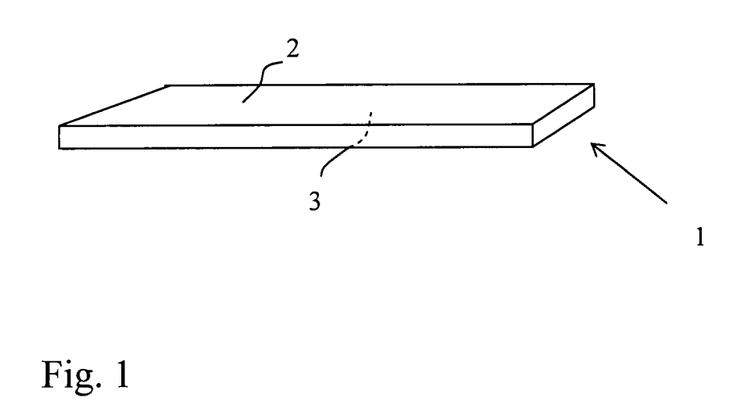
FIG. 1 is a perspective side view of a sample substrate, indicating the reaction site surface and the opposing substrate surface.

FIG. 1 illustrates schematically a sample substrate 1 for an optical assay arrangement, the sample substrate having a reaction site surface 2 and a substrate surface 3, located opposite each other. The reaction site surface of the substrate may further be provided with a pattern of protruding microstructures, e.g. micro posts (not illustrated), which may be arranged to form a capillary flow path for the sample. The size of the substrate is preferably adapted to form a suitable carrier for one or more reaction site areas for an optical assay, and a prior art microarray slide is rectangular, with a size of 25 mm×75 mm. The thickness of the substrate may be e.g. approximately 1 mm and the width and length e.g. between approximately 1 mm and 100 mm, forming an approximately rectangular or quadratic surface area. The material of the substrate may be a thermoplastic polymer, e.g. a cycloolefinpolymer or a cycloolefincopolymer, having suitable optical properties, e.g. regarding the transparency of the optical radiation, with an index of refraction typically between 1.5 and 1.6. A polymeric substrate may be manufactured by a polymer replication of a master structure, e.g. by injection molding. However, other substrate material may be used, e.g. glass or silicon, having suitable optical properties.

Figure 2:
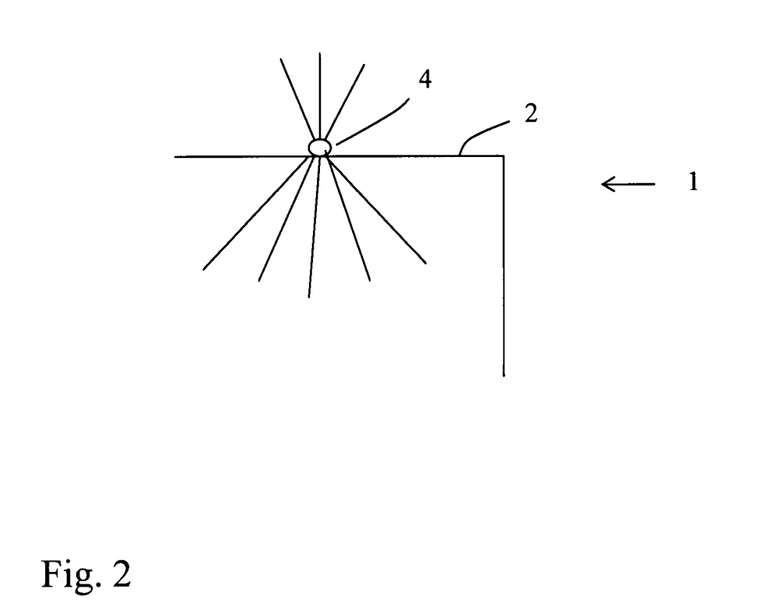
FIG. 2 illustrates the emission asymmetry of a fluorophore located on a reaction site surface of a polymeric sample substrate.

FIG. 2 illustrates schematically the excited electromagnetic rays emitted from a fluorophore 4 located on the reaction site surface 2 of a dielectric sample substrate 1. The emission is asymmetric due to the different optical properties of air and the substrate material, and the intensity of the emitted light is larger within the substrate than in the air. Since the substrate has a high transmittance of the wavelengths of the emitted rays, it is advantageous to detect the excited fluorescence light from the substrate side.

Figure 3:
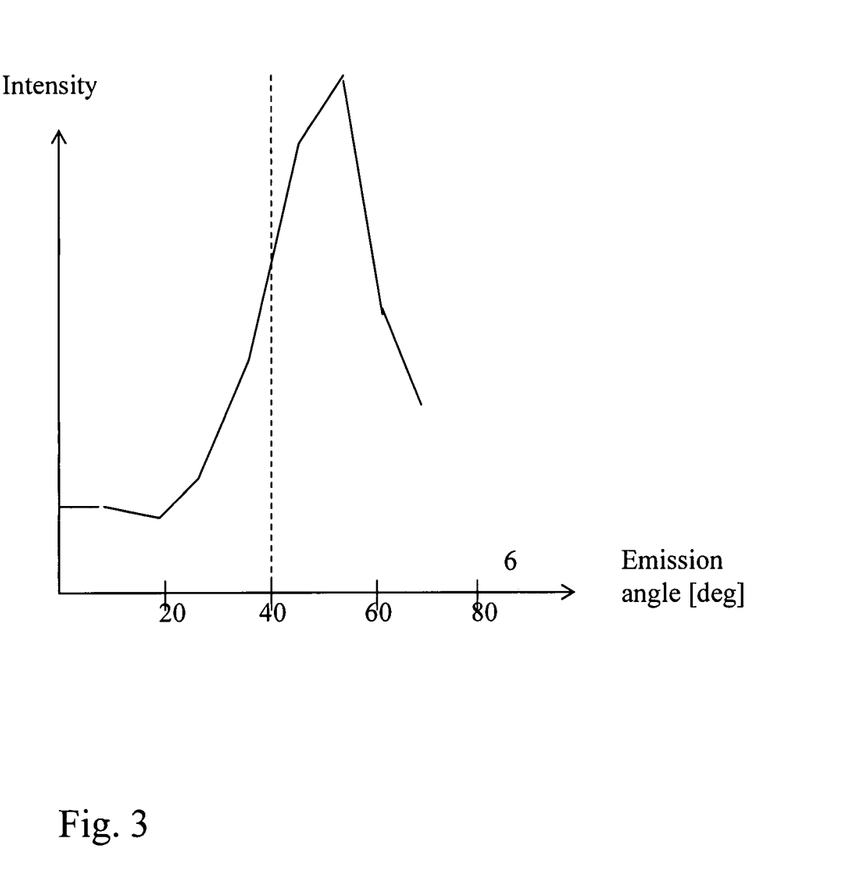
FIG. 3 is a graph schematically illustrating the fluorescence emission lobe of a fluorophore.

FIG. 3 is a graph schematically illustrating the intensity of the different emission angles from a thin layer of the fluorophore Cy-5™, the emission angle defined as the angle to the surface normal. (However, for a given emission angle, light will be emitted over 360°.) The graph indicates that the fluorescence emission is highly anisotropic, with a peak at an angle of approximately 50 degrees. This is an angle that is larger than the critical angle for total internal reflection for the substrate/air interfacing surface, since the critical angle of total internal reflection for a light ray propagating in a substrate material with a refractive index of 1.55 and impinging on the substrate/air interfacing surface is 40 degrees, according to the relationship (1) above. Therefore, most of the fluorescence light emitted within the substrate will impinge on the inner side of the substrate surface with an angle exceeding the critical angle for total internal reflection, and will be trapped inside the substrate. This light will, consequently, not reach a detector located outside the substrate surface in a controlled way. Some of the light trapped inside the substrate will eventually be refracted out of the substrate at the substrate edges, but this light will normally not reach the detector. If the reaction site surface is provided with protruding microstructures these may also affect the optical conditions for total internal reflection.

However, in a fluorescence reader according to this invention, the substrate surface is provided with total-internal-reflection suppressing means in order to release the captured total-internal-reflected rays by diffracting or refracting the rays, or by changing the refractive index-difference between the substrate material and air. Thereby, the detector device will be able to collect and detect a larger portion of the emitted fluorescence light, achieving a more reliable detection and a higher performance.

Figure 4:
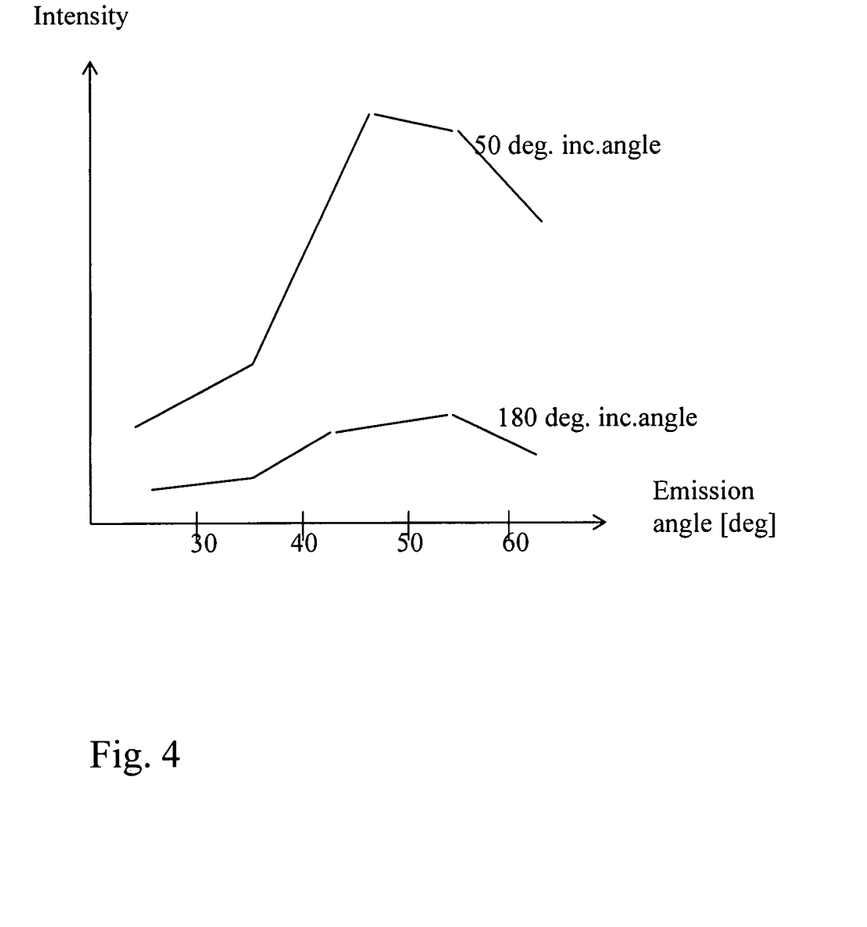
FIG. 4 is a graph schematically illustrating the fluorescence excitation efficiency at two different incidence angles of the exciting light, FIG. 5 schematically illustrates a cross section of a sample substrate and an exciting light source and a detector for the emitted fluorescent light, indicating the angle of incidence and the angle of emission.

FIG. 4 is a graph schematically illustrating the excitation efficiency dependency on the excitation incidence angle, showing the intensity of the emitted fluorescent light at two different angles of incidence of the illumination, i.e. 50 degrees and 180 degrees from the surface normal, respectively. The graph indicates the intensity at different emission angles in the interval between 30 and 60 degrees, with the light approaching the fluorophores from the substrate surface with an incidence angle of 50 degrees relative the surface normal, and the intensity at different emission angles with an incidence angle of 180 degrees, i.e. light approaching the fluorophores in a direction in parallel with said surface normal. Apparently, the excitation efficiency is larger at an incidence angle of 50 degrees, i.e. an angle of incidence that substantially coincides with the emission peak, which is illustrated in FIG. 3.

According to one embodiment of this invention, an increased emission efficiency is achieved by selecting the angle of incidence of the exciting radiation to coincide with the maximum fluorescence emission angle. This is accomplished by arranging a light source to direct exciting light rays into a substrate 1 to illuminate the fluorophoric layer 4 with an angle of incidence coinciding with the maximum emission angle. However, light rays impinging on the substrate surface 3 can not refract into the surface with an angle that is higher than the one given by the relationship (1): $\sin \alpha_{ref} = n1/n2 \times \sin \alpha_{in}$. Since $\alpha_{in}$ is less than 90 degrees, $\sin \alpha_{in}$ is less than 1. The air/substrate surface will typically have a value of n1/n2 being 1/1.55=0.65. Therefore, $\sin \alpha_{ref} < 0.65$ and $\alpha_{ref}$ can not exceed 40 degrees. Since the incidence angle relative the fluorophoric layer corresponds to the angle of refraction, the incidence angle will also be less than 40 degrees, which is smaller than the desired incidence angle of 50 degrees. In order to enlarge the angle of incidence of the exciting light rays, the fluorescence reader, according to this embodiment of the invention, will illuminate the substrate surface 3 through incidence-angle-controlling means provided on the substrate surface in the optical path of the impinging exciting light rays, thereby further increasing the performance by achieving an enlarged incidence angle relative the surface normal. The incidence angle controlling means will enlarge the angle of refraction, and, accordingly, also the angle of incidence, by diffracting or refracting the injected light rays, or by changing the refractive index difference between the substrate material and air.

Figure 5:
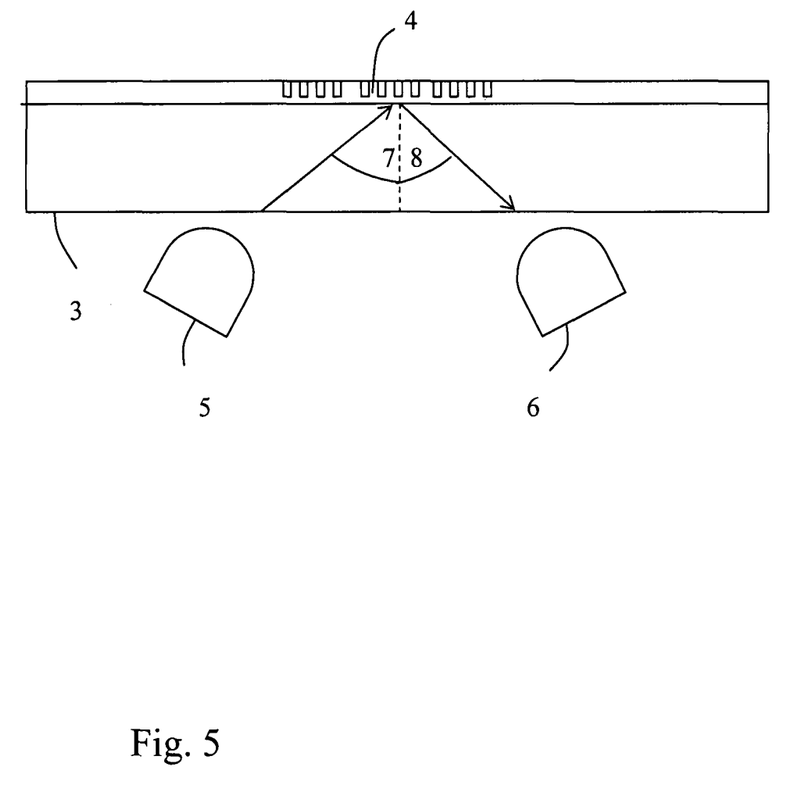

FIG. 5 schematically illustrates an optical assay arrangement, comprising a sample substrate provided with a fluorophoric layer 4 of e.g. Cy-5™ or TransFluoSpheres™ (Invitrogen Corporation). The fluorescence reader comprises a light source 5 illuminating the substrate surface 3 and a detector device 6 detecting light transmitted through said surface 3, the surface normal indicated by the dashed line. The intensity of the fluorescent light emitted from the fluorophoric layer 4 has a peak at the maximum emission angle 8, which is approximately 50 degrees, relative the indicated surface normal. Since this angle is larger than the critical angle of total internal reflection, which is approximately 40 degrees, at the inner side of the substrate surface 3, a large portion of the emitted fluorescent light will be trapped inside the substrate, therefore not reaching the detector 6. Thus, the detected intensity can be increased by applying total-internal-reflection suppressing means on the substrate surface, in the path of the emitted light rays, thereby releasing the trapped light rays from the substrate.

In order to achieve an enhanced emission, the light source 5 should inject exciting light rays into the substrate with an incidence angle 7, relative the indicated surface normal, substantially corresponding to said maximum emission angle 8 of 50 degrees. However, this angle cannot be obtained due to the refractive index relationship between air and the substrate material. In order to enlarge the incidence angle and increase the emission, incidence-angle-controlling means can be provided on the substrate surface, in the optical path of the injected light rays.

In a fluorescence reader according to this invention, total-internal-reflection suppressing means are provided on the substrate surface in the optical path of the emitted fluorescent light, in order to reduce the total-internal-reflection and release the trapped emitted light, preferably in the path of the maximum emission lobe of the emitted light. Additionally, in order to further increase the fluorescence emission, incidence-light-controlling means may be provided on the substrate surface in the path of the exciting light rays, thereby enlarging the incidence angle of the exciting light inside substrate to achieve an incidence angle substantially coinciding with the maximum emission angle of the fluorescence light.

FIGS. 6-8a schematically illustrates embodiments according to a first aspect of the invention, in which the total internal reflection suppressing means and the incidence angle controlling means are configured to diffract or refract the light rays in a desired direction. The total internal reflection suppressing means and the incidence angle controlling means comprise a relief structure 9 applied on the substrate surface 3 of the sample substrate, in the optical path of the emitted fluorescent light rays and of the exciting light rays. The surface relief structure is designed to be diffractive or refractive, and may comprise e.g. a grating or a facet-structure, providing a surface on which the light rays will diffract or refract into the desired directions.

Figure 6:
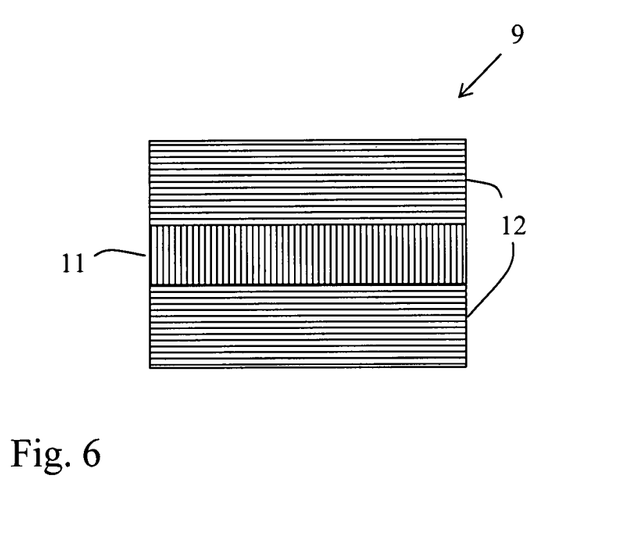
FIG. 6 is a view of a surface relief structure comprising both a total-internal-reflection-suppressing exit section and a incidence angle controlling entry section, provided on a substrate surface of a sample substrate, FIG. 7 schematically illustrates an enlarged example of the surface relief structure, FIG. 8a schematically illustrates a cross section of a substrate provided with a surface relief structured entry section and exit section.

FIG. 6 illustrates a first exemplary embodiment, in which the total-internal-reflection suppressing means and the incidence-angle-controlling means comprises a surface relief structure 9, divided in three sections, of which the first section 11 constitutes the incidence-angle-controlling means comprising an entry-section forming an inner channel designed to admit exciting light rays into the substrate with a suitable incidence angle, and the outer sections 12 constitutes total-internal-reflection suppressing means forming exit-sections allowing fluorescence light rays with an angle exceeding the critical angle for total internal reflection to be transmitted through the substrate surface. The exit-sections 12 are designed to release emitted fluorescent light rays having an emission angle both below and above the critical angle for total internal reflection from the substrate, and the entry-section 11 is designed to enlarge the incidence angle of the exciting rays inside the substrate, to exceed the refractive angle given by the relationship between the refractive indices of air and of the substrate.

The position of the entry-section and the exit-sections, respectively, is preferably adapted to the location of the fluorophores on the reaction site surface, e.g. by locating the entry section 11 directly under the fluorophores, since the fluorescent light is emitted with a low intensity at small angles of emission 8, and by locating the exit sections 12 to surround the entry section, especially in the path of the maximum emission lobe of the fluorescent light.

A further advantage with this invention is that a specific area of the reaction site area can be analysed by only detecting emitted fluorescent light from a specific, limited area of the surface relief structure, or by applying the total-internal reflection suppressing means to only cover a specific, limited area of the substrate surface.

The surface reliefs may be produced e.g. by e-beam lithography, grating ruling engines, holographic interference methods, diamond point turning, silicon micromachining etc, and the relief structure may e.g. be sinusoidal, triangular, or trapezoidal. The surface relief may be transferred onto a polymer substrate by replication methods from a master structure, like injection moulding. The surface reliefs can e.g. be formed as one- or two-dimensional pattern of facets, which may be designed to transmit the light rays undeviated or to focus the emitted light onto the detector device.

Figure 7:
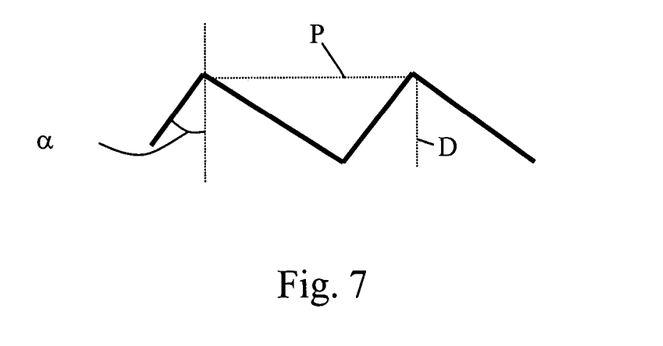

FIG. 7 illustrates a facet structure, having the facet angle α, depth D, and pitch, P, of which the depth and pitch are in the subµm-range, up to several hundreds of µm. If a coherent light source, e.g. a laser, is used, the surface relief will be of diffractive nature. If a non-coherent light source, e.g. a LED, is used, the surface relief will be of refractive nature. The light rays emitted from the fluorophores will impinge on the substrate surface with an incidence angle that varies over the substrate surface depending on the emission angel and on the position relative the fluorophores, e.g. of a line of fluorophores located directly above an inner channel 11, illustrated in FIG. 6. Therefore, according to a further embodiment of the relief structure, the design of the diffractive or refractive structure is arranged to vary over the surface of the exit section, in correspondence with the incidence angle of the impinging emitted light rays, on order to further improve the total-internal-reflection suppressing function.

According to a further embodiment of a fluorescence reader, in which the position of the light source is fixed relative the substrate, the design of the diffractive or refractive structure is arranged to vary over the surface of the entry section in correspondence with the intensity distribution of the exciting light beam, or in order to achieve focusing of the exciting light.

Figure 8A:
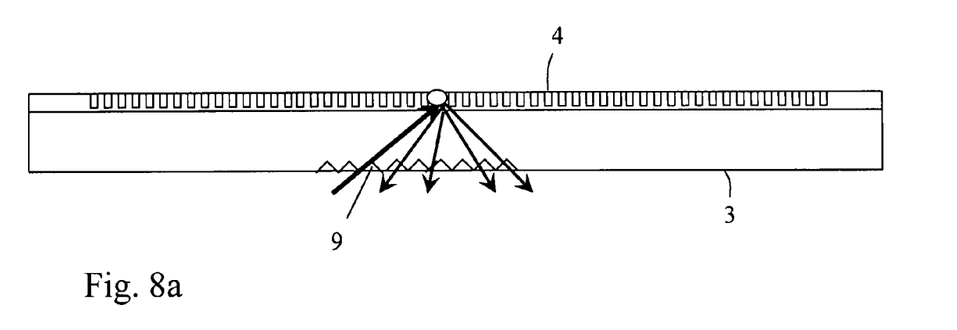

FIG. 8a is a cross-sectional view of a sample substrate, with a fluorophoric layer 4 and a substrate surface 3 provided with a surface relief structure 9, of which one section is functioning as total internal reflection suppressing means, and another section is functioning as incidence angle controlling means, through which exciting light rays and fluorescent emitted light rays are transmitted, respectively.

Figure 8B:
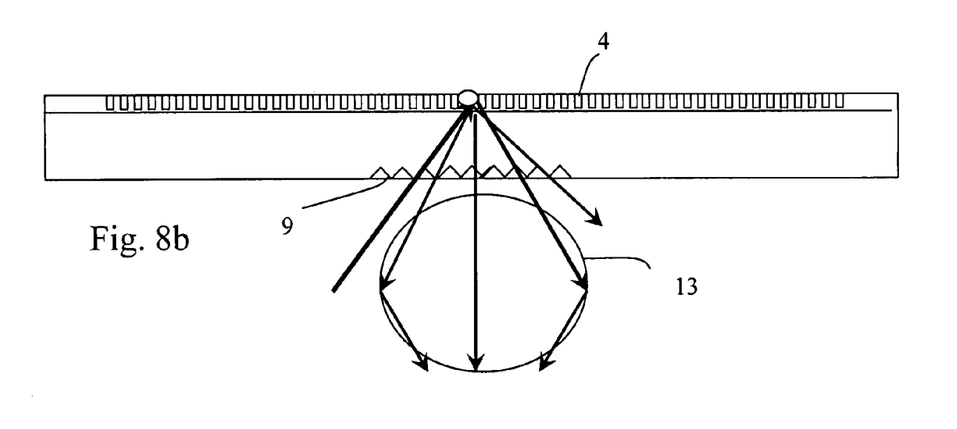
FIG. 8b illustrates the substrate of FIG. 8a, further provided with a light collecting lens device for the emitted light.

FIG. 8b illustrates a further embodiment of a fluorescence reader according to the first aspect, showing the sample substrate according to FIG. 8a, further provided with a light collecting lens 13 positioned to receive the fluorescent light transmitted through the surface relief 9, in order to increase the intensity of the emitted light reaching the detector device (not illustrated) and thereby further improving the performance.

Figure 9:
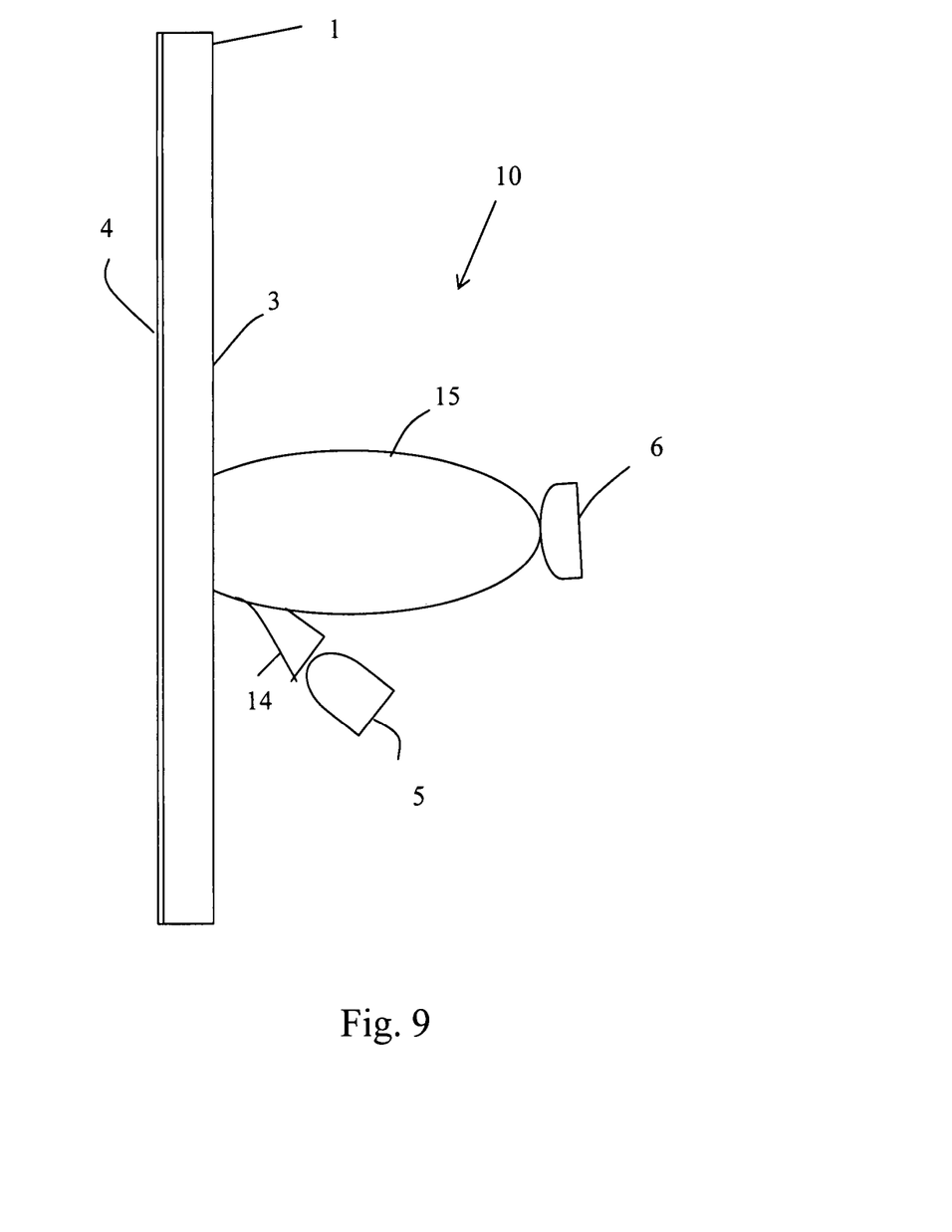
FIG. 9 illustrates a fluorescence reader comprising a total-internal-reflection suppressing light-collecting body provided with an input port functioning as a light directing device.

FIG. 9 schematically illustrates a fluorescence reader 10, suitable for an optical assay arrangement comprising a sample substrate 1 provided with a fluorophoric layer 4, according to a second aspect of the invention, in which the total-internal-reflection suppressing means comprises a light collecting body 15 of a suitable material, e.g. a polymeric material or glass. According to a first embodiment, the light-collecting body 15 has a refractive index that corresponds to, or is larger than, the refractive index of the substrate material. The light-collecting body is positioned in physical contact with the surface, preferably in optically wetting contact, in order to "open up" the substrate surface and to allow the fluorescent light rays having an emission angle that exceeds the critical angle for total internal reflection to escape the substrate and enter into the body 12. Additionally, the shape of the light-collecting body will collect and focus the fluorescent light rays, e.g. by means of total-internal-reflection on the inner surface of the body, to reach the detector device 6, mounted on the light-collecting body. Thus, the illustrated light-collecting body acts both as a total-internal-reflection suppressor and as a light collector. Thereby, the intensity of emitted fluorescent light reaching the detector device 6 will increase, and the performance of the optical assay arrangement will be improved.

According to a second embodiment, the light collecting body is provided with an input port 14 functioning as a light-directing device, which is arranged to control the direction of the light rays from the light source to guide the exciting light into the substrate 1, e.g. to achieve an incidence angle substantially coinciding with the maximum emission angle of the fluorescent light. The optical properties of the light-collecting body 15 allows exciting light rays to enter the substrate with an appropriate incidence angle relative the fluorophoric layer provided on the reaction site surface. Thereby, the fluorophoric layer is more favorable excited, and more fluorescent light will be emitted, thereby further improving the performance of the optical assay arrangement.

According to further embodiments, the light collecting body 15 is provided with one or more output ports (not illustrated in the figure), arranged to e.g. function as a beam dump for specularly reflected exciting light rays.

Figure 10:
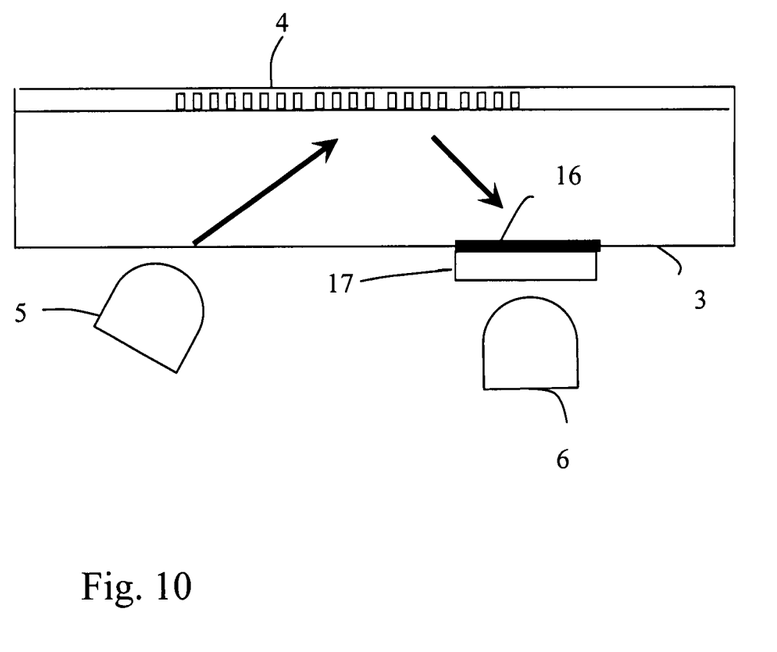
FIG. 10 shows an arrangement comprising a detector and lens, the lens provided with a total-internal-reflection suppressing wetting layer in physical contact with the substrate surface.

FIG. 10 schematically illustrates a fluorescence reader suitable for an optical assay arrangement comprising a sample substrate 1 provided with a fluorophoric layer 4, according to a third aspect of this invention, in which the total-internal-reflection suppressing means 16 is configured to change the refractive index-difference at the surface, by comprising an optically wetting layer of a suitable material. Since $\sin \alpha_{in(TIR)} = n2/n1$, as follows from the relationship (1)

above, more fluorescence light can be transmitted through the surface if the refractive index difference is reduced, such that n2/n1 is increased.

According to a first embodiment, the fluorescence reader comprises a light source 5, a detector 6 and a lens device 17, which is positioned to focus emitted fluorescent light onto the detector 6. The lens device 17 is provided with total-internal-reflection suppressing means 16 comprising a layer of a suitable material, having a suitable refractive, positioned in physical contact with the substrate surface 3. The material of the layer is preferably a soft polymer, e.g. silicon, epoxy, polyurethane or acrylate, which is applied as an optically wetting layer on the surface of the lens device 17, with no air between the layer and the surface. Thereby, the light rays propagating to the lens will not pass any air layer, which would cause reflection losses to occur at high angles. An additional advantage with selecting a soft polymeric material is that it is capable of forming an optically wetting layer on a surface that is not completely even or plane. Further, the material of the layer is selected to have suitable light transmitting properties, e.g. low fluorescence and low scattering of the transmitted emitted or exciting light rays, and the thickness of the layer 16 can be between a few μm and a few mm. A suitable value of the refractive index of the layer is between the values of the refractive index of the polymeric substrate material and of the lens device, respectively, the refractive index of the lens device being the largest. The total-internal-reflecting suppressing optically wetting layer 16 docked in physical contact with the substrate surface 3 releases the fluorescence rays from being trapped into the substrate, and enables a larger portion of the emitted rays to be collected by the detector 6.

The light source 5 is arranged to illuminate the substrate surface 3 of the sample substrate 1, and the detector device 6 is arranged to detect fluorescent light emitted from the fluorophoric layer 4 on the reaction site surface of the sample substrate and transmitted through the substrate surface 3. The light source 5 injects exciting light rays into substrate, and the maximum emission angle of the fluorescent light normally exceeds the angle for total internal reflection. However, the optically wetting layer 16 is applied as a total-internal-reflection suppressing means on the lens device 17 in order to increase the intensity of the light escaping through the surface by increasing the angle for total internal reflection.

According to an alternative embodiment, not illustrated in the figure, the optically wetting layer 16 is applied directly on a detector device 6, in case the detector device is adapted to collect the emitted light without any focusing means.

Preferably, the detector device is positioned such that the optically wetting layer is docked in physical contact with the substrate surface 3.

Further, the optically wetting layer 16 may cover substantially the entire lens 17 or detector device 6, or, alternatively, a suitable part of the surface of the detector 6 or lens 17, depending on the configuration of the optical assay arrangement.

According to an alternative embodiment, not illustrated in the figure, incidence angle controlling means is applied on the substrate surface 3, in order to enlarge the incidence angle of the exciting light rays relative the surface normal by changing the diffractive index difference at the surface. Since the incidence angle corresponds to the angle of refraction, which is given by the relationship $\sin \alpha_{ref} = n1/n2 \times \sin \alpha_{in}$, a change in the refractive index difference will affect the incidence angle. The incidence angle controlling means, according to this embodiment, comprises an optically wetting layer of a material, having a suitable refractive index, applied on the substrate surface in the optical path of the injected exciting light rays. If the refractive index of the optically wetting layer is larger than the refractive index of air, n1/n2 will increase, which will result in an enlarged $\alpha_{ref}$ and an enlarged incidence angle. The resulting incidence angle may preferably coincide with the maximum emission angle of the fluorescent, such that more fluorescent light will be emitted. The optically wetting layer may, alternatively, be applied on the surface of a light-directing device (not illustrated in the figure) arranged to control the direction of the exciting light rays.

According to a fourth aspect of the invention, the total-internal-reflection suppressing means comprises both a surface relief structure 9, according to the first aspect of the invention, as described with reference to FIGS. 6-8, and a light collecting body 15 according to the second aspect, as described with reference to FIG. 9. The light collecting body is preferably located in close proximity to the substrate surface, e.g. at a distance less than approximately 1 mm from the surface. By combining a surface relief structure 9 and a light collecting body 15, an improved suppression of the total-internal-reflection is achieved, while an improved collection of the emitted light is provided by means of the light collecting body.

In order to further increase the performance of the optical assay arrangement, a fluorescence reader implemented according to any of the aspects of the invention, as described above, is provided with suitable filter, e.g. spectral filter and polarization filters, in order to prevent any exciting light from reaching the detector. Since a part of the exciting light rays will be reflected, transmitted through the substrate and released from the substrate surface to be detected by the detector device, the detector device is preferably provided by spectral filters removing the wavelengths of the exciting light rays. However, the spectrum of the exciting light rays, which may be light from e.g. a laser diode or a light emitting diode (LED), normally has a tail that extends into the wavelength region of the emitted fluorescent light, which depends on the type of fluorophores in the fluorophoric layer. Since the wavelengths of the fluorescent light cannot be removed by detector filters, the exciting light source is preferably provided with spectral filters removing the tail. Thus, according to further exemplary embodiments of the fluorescence reader, the detector is provided with spectral filters removing the wavelengths of the exciting light rays and of any other unwanted light sources, and the light source is provided with spectral filters removing the wavelengths coinciding with the fluorescent light. Therefore, the cut-off frequency of the detector filtering means has to be adapted to the cut-off frequency of the light source filtering means, avoiding any overlap between the wavelength ranges of the exciting light and the detected light, thereby further improving the efficiency of the fluorescence reader.

In order to prevent any exciting light from reaching the detector, another exemplary embodiment of the fluorescence reader is arranged to use different, orthogonally placed, geometrical planes for the exciting light and for the measurement of the emitted, fluorescent light, e.g. a geometric yz-plane for the excitation and a geometric xz-plane for the measurement of the emission.

According to a further embodiment of the fluorescence reader, the exciting light rays can be prevented from reaching the detector by providing the light source, if needed, and the detector with polarizing filters. If the sample substrate has a low birefringence, one exemplary setup would be to align the two polarizers perpendicularly to each other. Thereby, only fluorescent light polarized in parallel with the polarizing filter of the detector will be detected. Alternatively, if the birefringence is varying and not negligible, one of the polarizers has to be rotatable to a suitable angle to remove the exciting light, thereby achieving a further improved performance of the fluorescence reader.

Thus, by providing a scanning or an imaging fluorescence reader with suitable total-internal-reflection suppressing means, incidence-light controlling means, lenses and light-directing devices, as well of spectral and/or polarizing filtering, as described above, a high performance optical assay arrangement can be achieved.

However, the invention is not restricted to the described embodiments in the figures, but may be varied freely within the scope of the appended claims.

The invention claimed is:

1. In combination, a fluorescence reader and a sample substrate, said substrate having a reaction site-surface and a substrate surface opposed to said reaction site-surface wherein the reaction site comprises disposed thereon,
    said fluorescence reader comprising:
        a light source positioned to inject exciting light rays into the substrate surface; and
        a detector device positioned to detect fluorescent light emitted from the fluorophores disposed on the reaction site-surface and transmitted through the substrate surface, wherein said substrate surface is provided with a total-internal-reflection-suppressing means located in an optical path of the emitted fluorescent light for increasing transmission through the substrate surface for detection by the detector device, said total-internal-reflection-suppressing means being arranged to release emitted fluorescent light trapped within the sample substrate and comprising a surface relief structured exit-section on said substrate surface, said exit-section having a faceted surface designed to either diffract or refract the emitted fluorescent light out of the substrate.

2. The combination according to claim 1, wherein said light source is arranged to inject exciting light rays into the substrate surface with an incidence angle substantially coinciding with the maximum emission angle of the emitted fluorescent light wherein the incident angle is measured relative to the normal of the reaction site surface.

3. The combination according to claim 2, wherein said substrate surface is provided with an incidence-angle-controlling means located in the optical path of the exciting light rays.

4. The combination according to claim 3, wherein said incidence-angle-controlling means comprises an optically wetting layer having a suitable refractive index.

5. The combination according to claim 4, wherein said optically wetting layer comprises a soft polymeric material.

6. The combination according to claim 3, wherein said incidence-angle-controlling means comprises a surface relief structured entry-section designed to admit exciting light into the sample substrate with the incidence angle, wherein said incidence angle is enlarged and wherein the incident angle is measured relative to the normal of the reaction site surface.

7. The combination according to claim 6, wherein said surface relief structured entry-section comprises a diffractive structure.

8. The combination according to claim 6, wherein said surface relief structured entry-section comprises a refractive structure.

9. The combination according to claim 1, wherein said surface relief structured exit-section is further designed to focus the emitted fluorescent light.

10. The combination according to claim 1, wherein said surface relief structured-exit section comprises a diffractive structure.

11. The combination according to claim 1, said surface relief-structured exit section comprises a refractive structure.

12. The combination according to claim 1, wherein the design of a surface relief structure is arranged to vary over a surface of the structure relief structured exit-section in correspondence with the varying emission angle of impinging fluorescent light.

13. The combination according to claim 1, wherein the position and extension of the surface relief structured exit-section determines the position and extension of an analyzed reaction site area.

14. The combination according to claim 1, wherein a light collecting lens device is positioned to receive the emitted fluorescent light transmitted through the substrate surface.

15. The combination according to claim 1, wherein a light-collecting body is located in close proximity to the surface relief structured exit-section provided on said substrate surface.

16. The combination according to claim 1, wherein said detector device is provided with spectral filtering means arranged to prevent detection of the wavelengths of the exciting light rays.

17. The combination according to claim 1, wherein said detector device is provided with polarization filtering means.

18. The combination according to claim 1, wherein said light source is provided with spectral filtering means arranged to prevent transmission of the wavelengths coinciding with the emitted fluorescent light.

19. The combination according to claim 1, wherein said sample substrate is made of a polymeric material.

20. The combination according to claim 1, wherein said reaction site-surface is arranged to form lines and/or spots of said fluorophores.

21. The combination according to claim 1, wherein the reaction site-surface is provided with a pattern of protruding microstructures.

22. The combination according to claim 21, wherein said protruding microstructures comprise micro posts enabling a capillary flow.

23. In combination, a fluorescence reader and a sample substrate, said substrate having a reaction site-surface and a substrate surface opposed to said reaction site-surface wherein the reaction site-surface comprises fluorophores disposed thereon,
    said fluorescence reader comprising:
        a light source positioned to inject exciting light rays into the substrate surface; and
        a detector device positioned to detect fluorescent light emitted from the fluorophores disposed on the reaction site-surface and transmitted through the substrate surface, wherein said substrate surface is provided with a total-internal-reflection-suppressing means located in an optical path of the emitted fluorescent light for increasing transmission through the substrate surface for detection by the detector device wherein said total-internal-reflection-suppressing means comprises a light-collecting body positioned in optically wetting contact with the exterior of said substrate surface, said contact being sufficient such that no air layer is formed between said light-collecting body and the exterior of said substrate surface and in which the light-collecting body is designed to collect and transmit light by means of total internal-reflection.

24. The combination according to claim 23, wherein said light-collecting body is substantially ellipsoid-shaped.

25. The combination according to claim 23, wherein said light-collecting body is provided with an input port for the exciting light rays.

26. The combination according to claim 23, wherein said light-collecting body is provided with at least one output port.

27. The combination according to claim 23, wherein said light-collecting body has a refractive index that substantially corresponds to, or is larger than, the refractive index of the sample substrate.

28. In combination, a fluorescence reader and a sample substrate, said substrate having a reaction site-surface and a substrate surface opposed to said reaction site-surface wherein the reaction site-surface comprises fluorophores disposed thereon,
   said fluorescence reader comprising:
      a light source positioned to inject exciting light rays into the substrate surface; and
      a detector device positioned to detect fluorescent light emitted from the fluorophores disposed on the reaction site-surface and transmitted through the substrate surface, wherein said substrate surface is provided with a total-internal-reflection-suppressing means located in an optical path of the emitted fluorescent light for increasing transmission through the substrate surface for detection by the detector device, wherein said total-internal-reflection-suppressing means comprises an optically wetting layer having a suitable refractive index, said optically wetting layer being in sufficient physical contact with the exterior of said substrate surface such that no air layer is formed between said wetting layer and said substrate surface and wherein at least a portion of the optically wetting layer is attached to a lens device arranged to focus the emitted fluorescent light on the detector device and wherein the optically wetting layer has a refractive index that is higher than the refractive index of the substrate surface and lower than the refractive index of the lens device.

29. The combination according to claim 28, wherein said optically wetting layer is attached to one of the substrate surface and the detector device.

30. A method of detecting the fluorescence of a sample substrate using a fluorescence reader, said method comprising the steps of:
   a) injecting exciting light rays into a substrate surface with a light source positioned to inject exciting light rays into the substrate surface wherein said substrate surface is opposed to a reaction site-surface;
   b) detecting fluorescent light emitted by fluorophores disposed on the reaction-site surface with a detector device positioned to detect the fluorescent light which is emitted by said fluorophores from the reaction site-surface and transmitted through the substrate surface;
   c) providing said substrate surface with a total-internal-reflection-suppressing means located in an optical path of the fluorescent light for increasing transmission through the substrate surface for detection by the detector device, said total-reflection-suppressing means providing step including the step of machining a surface relief exit-section including a faceted surface into said substrate surface designed to either diffract or refract emitted fluorescent light from said fluorophores and in which said fluorescence reader is positioned in an optical assay arrangement.

31. The method according to claim 30, wherein said injecting step and said detection step of the emitted fluorescent light are performed in different geometrical planes.

* * * * *